US006951954B1

(12) United States Patent
Giardino et al.

(10) Patent No.: US 6,951,954 B1
(45) Date of Patent: Oct. 4, 2005

(54) CONTINUOUS PROCESS FOR PRODUCING BIS(3-HYDROXYPROPYL) TEREPHTHALATE

(75) Inventors: Carl J. Giardino, Hixson, TN (US); David B. Griffith, Houston, TX (US); Chungfah Howard Ho, Kinston, NC (US); James M. Howell, Greenville, NC (US); Michelle Hoyt Watkins, Waynesboro, VA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 536 days.

(21) Appl. No.: 09/503,599

(22) Filed: Feb. 11, 2000

(51) Int. Cl.$^7$ ............................................. C07C 67/02
(52) U.S. Cl. ........................... 560/92; 560/91; 562/89; 562/92; 562/103
(58) Field of Search .......................... 562/89, 103, 92; 560/91, 92

(56) References Cited

U.S. PATENT DOCUMENTS

| | | | |
|---|---|---|---|
| 2,727,882 A | 12/1955 | Vodonik | |
| 2,829,153 A | 4/1958 | Vodonik | 260/470 |
| 2,932,625 A | 4/1960 | Burton et al. | 260/75 |
| 2,933,476 A | 4/1960 | Fisher | 260/75 |
| 2,973,341 A | 2/1961 | Hippe et al. | 260/75 |
| 3,054,776 A | 9/1962 | Higgins | 260/75 |
| 3,167,531 A | 1/1965 | Parker et al. | 260/75 |
| 3,192,184 A | 6/1965 | Brill | 260/75 |
| 3,438,942 A | 4/1969 | Scheller et al. | 260/75 |
| 3,441,540 A * | 4/1969 | Muller et al. | |
| 3,506,622 A | 4/1970 | Higgins | 260/75 |
| 3,534,082 A * | 10/1970 | Armstrong | |
| 3,609,125 A | 9/1971 | Fujimoto et al. | 260/75 |
| 5,434,239 A | 7/1995 | Bhatia | 528/274 |
| 5,466,776 A | 11/1995 | Krautstrunk et al. | 526/68 |
| 5,510,454 A | 4/1996 | Stouffer et al. | 528/308.1 |
| 5,540,868 A | 7/1996 | Stouffer et al. | 264/13 |
| 5,552,513 A | 9/1996 | Bhatia | 528/308.3 |
| 5,599,900 A | 2/1997 | Bhatia | 528/491 |
| 5,633,018 A | 5/1997 | Stouffer et al. | 425/8 |
| 5,663,281 A | 9/1997 | Brugel | 528/272 |
| 5,670,606 A | 9/1997 | Stouffer et al. | 528/272 |
| 5,677,415 A | 10/1997 | Bhatia | 528/176 |
| 5,688,898 A | 11/1997 | Bhatia | 528/272 |
| 5,763,104 A | 6/1998 | Stouffer et al. | 528/503 |
| 5,786,443 A | 7/1998 | Lowe | 528/272 |
| 5,811,496 A | 9/1998 | Iwasyk et al. | 525/444 |
| 5,840,957 A * | 11/1998 | Kurian et al. | |
| 5,849,849 A | 12/1998 | Bhatia | 525/444 |
| 5,891,985 A | 4/1999 | Brugel | 528/283 |
| 5,990,265 A | 11/1999 | Blanchard et al. | 528/272 |
| 6,093,786 A | 7/2000 | Kelsey | |
| 6,255,442 B1 | 7/2001 | Kurian et al. | |
| 6,277,947 B1 | 8/2001 | Kelsey et al. | |
| 6,281,325 B1 | 8/2001 | Kurian et al. | |
| 2001/0029289 A1 | 10/2001 | Kelsey et al. | |

FOREIGN PATENT DOCUMENTS

| | | | |
|---|---|---|---|
| EP | 0 547 553 | 6/1993 | C08G 63/85 |
| EP | 1 046 662 A1 | 10/2000 | |
| WO | WO99/54040 | 4/1999 | B01J 31/38 |

OTHER PUBLICATIONS

Traub et al., Mechanical Properties of Fibers Made of Polytrimethylene Terephthalate, *Chemical Fibers International*, 45, 110-111, Apr. 1995.

Schauhoff et al.,, New Developments in the Production of Polytrimethylene Terephthalate (PTT), *Man-Made Fiber Year Book*, Sep. 1996.

Written Opinion from counterpart application PCT/US 00/21783, 2001.

* cited by examiner

*Primary Examiner*—Shailendra Kumar
(74) *Attorney, Agent, or Firm*—Nancy S. Mayer; Lucas K. Shay; Mark D. Kuller

(57) ABSTRACT

A process for the continuous production of at least one of bis(3-hydroxypropyl) terephthalate and low molecular weight oligomers of 1,3-propanediol and terephthalic acid is disclosed. According to the process, preheated 1,3-propanediol (about 150° C. to about 200° C.) and preheated lower dialkyl esters of terephthalic acid (about 150° C. to about 220° C.) are combined in a mole ratio of about 1.2:1 to about 2.3:1 and fed to an ester exchange vessel where the mixture undergoes a continuous transesterification reaction. The liquid reaction mixture is continuously heated and mixed, at a temperature of about 215° C. to about 250° C., and a pressure of about 800 mm Hg to about 1,000 mm Hg. Gaseous reaction products are continuously separated from the liquid reaction mixture, and a stream of liquid reaction products containing bis(3-hydoxypropyl) terephthalate and low molecular weight oligomers of 1,3-propanediol and terephthalic acid is continuously removed from a base portion of the ester exchange vessel.

33 Claims, 1 Drawing Sheet

CONTINUOUS PROCESS FOR PRODUCING BIS(3-HYDROXYPROPYL) TEREPHTHALATE

FIELD OF THE INVENTION

The present invention relates to a continuous process for the production of a mixture of bis(3-hydroxypropyl) terephthalate monomer and low molecular weight oligomers of 1,3-propanediol and terephthalic acid from 1,3-propanediol and dimethylterephthalate. The bis(3-hydroxypropyl) terephthalate monomer/oligomer mixture may be used as a feed material in a continuous polymerization process for the production of poly(1,3-propylene terephthalate).

BACKGROUND OF THE INVENTION

Batch processes for the production of bis(hydroxyalkyl) terephthalate esters are known. For example, Doerr et al., U.S. Pat. No. 5,340,909 discloses a batch process for the manufacture of poly(1,3-propylene terephthalate), including a batch ester interchange reaction in which 1,3-propanediol is reacted with a lower dialkyl ester of terephthalic acid.

Continuous transesterification processes are known for the production of bis(2-hydroxyethyl) terephthalate. For example, Vodonik, U.S. Pat. No. 2,829,153, discloses a continuous process for the production of bis(2-hydroxyethyl) terephthalate and its low molecular weight oligomers from ethylene glycol and dimethylterephthalate.

It would be highly desirable to provide a continuous ester exchange process for the production of bis(3-hydroxypropyl) terephthalate and its low molecular weight oligomers from 1,3-propanediol and dimethylterephthalate. The present invention provides such a process.

SUMMARY OF THE INVENTION

The invention comprises a process for the continuous production of at least one of bis(3-hydroxypropyl) terephthalate and low molecular weight oligomers of 1,3-propanediol and terephthalic acid, comprising:

(a) preheating 1,3-propanediol to a temperature of about 150° C. to about 200° C.;

(b) preheating one or more lower dialkyl esters of terephthalic acid to a temperature of about 150° C. to about 220° C.;

(c) combining the preheated 1,3-propanediol with the preheated terephthalic acid esters to form a mixture having a mole ratio of 1,3-propanediol to terephthalic acid ester of about 1.2:1 to about 2.3:1 and maintaining the temperature of the mixture at about 150° C. to about 220° C.;

(d) continuously feeding the preheated 1,3-propanediol/terephthalic acid ester mixture through at least one inlet to an ester exchange vessel where the mixture undergoes a continuous transesterification reaction to form a liquid reaction mixture and gaseous reaction products;

(e) continuously heating and mixing the liquid reaction mixture, whereby the temperature of the mixture in a base portion of the ester exchange vessel is maintained at about 215° C. to about 250° C. and the pressure in a base portion of the ester exchange vessel is maintained at about 800 mm Hg to about 1,000 mm Hg (10664 to 133322 Pa), thereby continuing the transesterification reaction to form liquid reaction products and gaseous reaction products;

(f) continuously separating the gaseous reaction products from the liquid reaction mixture in a separating portion of the ester exchange vessel which is above the base portion; and (g) continuously removing a stream of liquid reaction products from the base portion of the ester exchange vessel, the stream comprising at least one of bis(3-hydroxypropyl) terephthalate and low molecular weight oligomers of 1,3-propanediol and terephthalic acid.

DETAILED DESCRIPTION OF THE PREFERRED EMBODIMENTS

According to the process of the invention, 1,3-propanediol and one or more lower dialkyl esters of terephthalic acid are reacted to form bis(3-hydroxypropyl) terephthalate and low molecular weight oligomers of 1,3-propanediol and terephthalic acid having an average degree of polymerization of about 1 to about 15. While lower dialkyl esters of terephthalic acid other than dimethylterephthalate may be used in the process of the invention, for simplicity, the remainder of the description refers only to dimethylterephthalate.

Figure 1:
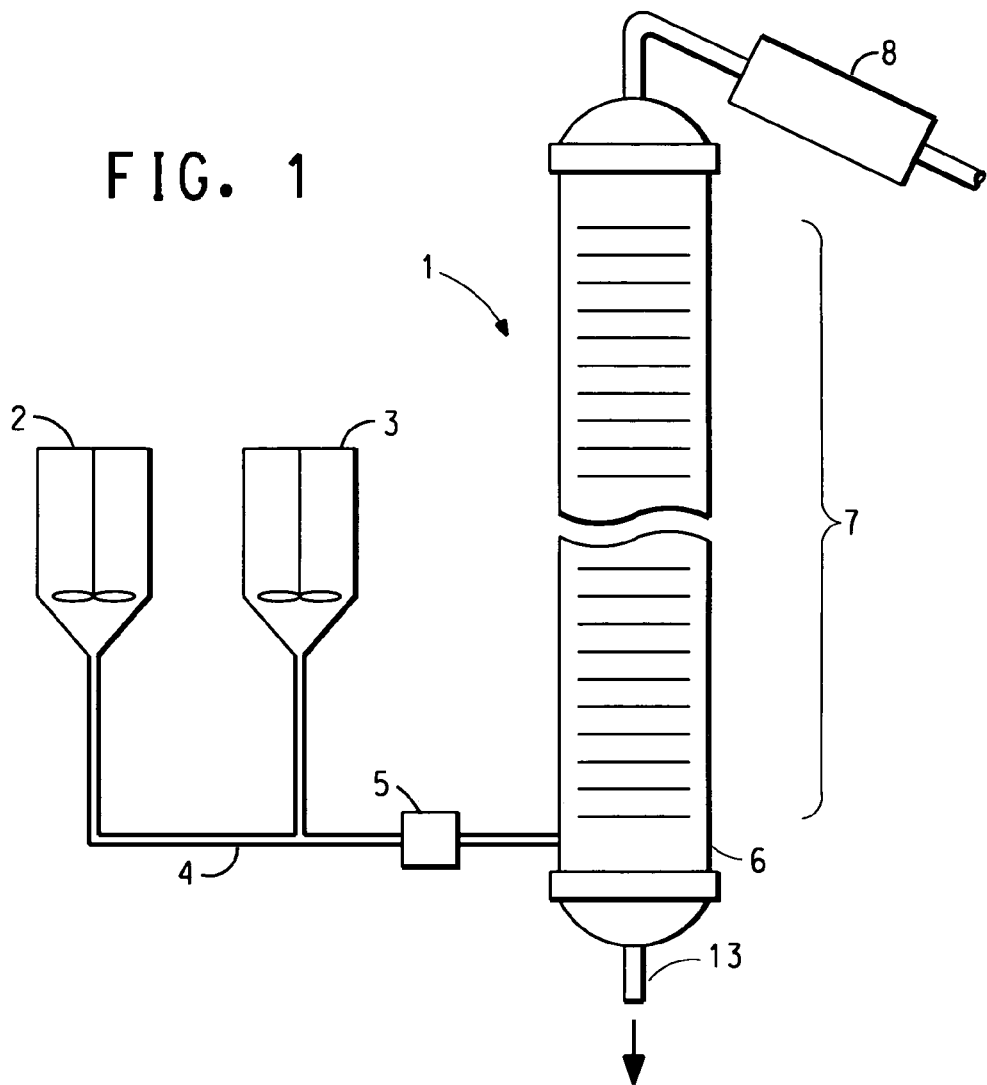
FIG. 1 is a schematic representation of an apparatus useful in carrying out the process of the invention.

As shown in FIG. 1, a mixture of 1,3-propanediol and transesterification catalyst is fed to ester exchange column 1 from tank 2, and dimethylterephthalate is fed from tank 3, both via temperature-controlled feed lines 4.

The 1,3-propanediol is mixed with a catalyst, preferably prior to mixing with dimethylterephthalate. Catalysts useful in the process of the invention include organic and inorganic compounds of titanium, lanthanum, zinc and cobalt, such as oxides, carbonates, phosphorus derivatives, and alkyl, aryl and acyl derivatives, and the like. Examples of such catalysts include tetraisopropyl titanate, tetraisobutyl titanate, lanthanum acetylacetonate and cobalt acetate. Titanium catalysts, such as tetraisopropyl titanate and tetraisobutyl titanate are preferred and are added to the 1,3-propanediol in an amount sufficient to yield 20 to 90 ppm of titanium by weight based on the weight of poly(1,3-propylene terephthalate) formed in subsequent processing.

The catalyzed 1,3-propanediol is preheated to a temperature of about 150° C. to about 200° C., preferably about 185° C., prior to mixing with dimethylterephthalate. The dimethylterephthalate is preheated to a temperature of about 150° C. to about 220° C., preferably about 185° C., prior to mixing with catalyzed 1,3-propanediol. The preheated catalyzed 1,3-propanediol is mixed with the preheated dimethylterephthalate by means of static mixer 5 in the feed line. Optionally, preheating is continued after mixing, such that the catalyzed 1,3-propanediol/dimethylterephthalate mixture reaches a temperature of about 150° C. to about 220° C., preferably about 200° C. to about 220° C., prior to being fed to the ester exchange vessel.

The mole ratio of 1,3-propanediol to dimethylterephthalate is about 1.2:1 to 2.3:1, preferably about 1.3:1 to 1.7:1, and most preferably about 1.5:1 in the mixture that is fed to the ester exchange vessel.

In a preferred embodiment of the invention, the ester exchange vessel has three integral sections. The base portion of the vessel is the calandria 6, above which is bubble cap column 7 and one or more condensers 8. The calandria functions as a heat exchanger to heat the liquid reactants to a temperature of about 215° to 250° C., preferably about 230° to 240° C., and most preferably about 235° C.

The calandria is jacketed and heated by means of a gaseous or liquid heating medium, e.g., Dowtherm vapor. The calandria supplies all of the heat for the ester exchange column. If desired, a stream of the liquid reaction mixture can be withdrawn from the exchange vessel, passed through the external heater and heated, and then fed back to the exchange vessel to cause mixing.

Figure 2:
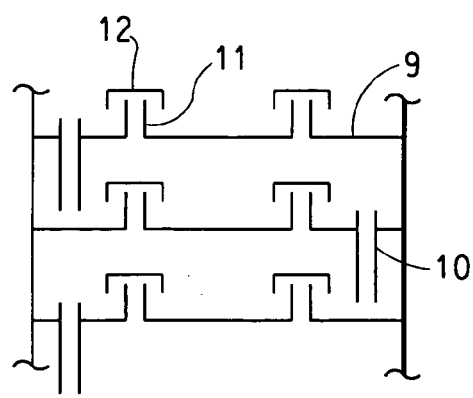
FIG. 2 is a schematic representation of a section of a bubble cap column useful in carrying out the process of the invention.

As shown in FIG. 2, bubble cap plate section 7, also referred to as the tray section or column, has a plurality of bubble cap plates (or trays) 9, each one extending completely across the column and spaced apart vertically from one another by a distance of typically about one foot. Each bubble cap plate 9 holds a constant level of liquid on the plate during operation. Each plate 9 as a plurality of bubble caps which are evenly distributed across the plate. The bubble caps allow hot vapor to rise through the plates and up the column. Each bubble cap has a chimney 11 and a cap 12 which is notched along the lower edge and fits down onto plate 9. Vapor traveling up though a chimney 11 reverses direction when it reaches the lower surface of cap 12. The vapor then pushes the liquid under cap 12 down until it is below the notches and then bubbles up through the liquid around the outside of the bubble cap. Plates 9 also have baffles to direct the flow of liquid 1,3-propanediol and dimethylterephthalate across the plate and around the bubble caps and a downcomer 10 to carry the liquid from one plate to the one below. Additional information regarding bubble cap columns is available, e.g., from R. H. Perry and D. W. Green, Perry's Chemical Engineers' Handbook, $7^{th}$ ed., Section 14 (The McGraw-Hill Companies, 1997).

Due to the structure of bubble cap column 7, there is a gradual step-wise decrease in pressure from below the first plate to above the uppermost plate in the ester exchange column. The pressure at the base of the column, i.e., above the liquid level in the calandria and below the first plate, is maintained at a pressure of about 800 mm Hg to about 1,000 mm Hg (106,640 to 133,322 Pa), preferably about 850 to 950 mm Hg (113,305 to 126,635 Pa). The pressure at the top of the column is at or near atmospheric pressure because the top of the exchanger is vented to the atmosphere.

The 1,3-propanediol/dimethylterephthalate mixture may be injected into the ester exchange column at various points at or below about the midpoint of the tray section. For example, the 1,3-propanediol/dimethylterephthalate mixture may be injected at the base of the exchanger (calandria), or onto a tray located approximately one quarter of the distance between the bottom and the top of the exchanger (hereinafter the "quarterpoint"), or onto a tray located at approximately the midpoint of the exchanger. The injection point and mole ratio are adjusted in order to minimize unconverted dimethylterephthalate and acrolein and allyl alcohol generation. The preferred process is to use a mole ratio of about 1.5:1 1,3-propanediol to dimethylterephthalate and to inject the 1,3-propanediol/dimethylterephthalate mixture into the base of the exchanger column below the first tray. Alternatively, a mole ratio of up to 2.0 moles of 1,3-propanediol per mole of dimethylterephthalate is used, and the 1,3-propanediol/dimethylterephthalate mixture is injected at the quarterpoint or midpoint of the exchanger. In this latter process, a higher mole ratio is needed to prevent higher boiling monomer from staying on the trays. This alternate process has been found to reduce the unconverted dimethylterephthalate but requires that more 1,3-propanediol be recovered in the prepolymerization step.

In yet another alternative, a mixture of preheated, catalyzed 1,3-propanediol and preheated dimethylterephthalate is injected into the base of the exchanger, and additional virgin 1,3-propanediol, typically at ambient temperature, is injected at the quarterpoint of the exchange column. In this embodiment, the mixture that is injected into the base of the exchanger has a lower mole ratio of 1,3-propanediol to dimethylterephthalate and a higher catalyst concentration than the mixture used in previously described embodiments, such that the overall mole ratio and catalyst concentration remain within the above-described ranges, after taking into account the additional 1,3-propanediol that is injected at the quarterpoint. In still another alternative, preheated dimethylterephthalate and preheated catalyzed 1,3-propanediol are injected into the exchanger separately without premixing. For example, the dimethylterephthalate is injected into the base of the exchanger, and the catalyzed 1,3-propanediol is injected at the quarterpoint.

At least one condenser 8 is provided for condensing the methanol vapor and other gaseous by-products produced by the transesterification reaction. A portion of the condensed methanol can be refluxed back to the bubble cap column to control the top tray temperature. Any remaining condensate is removed from the process.

The methanol vapor exiting the ester exchange column typically contains other reaction by-products such as acrolein and allyl alcohol. It is desirable that the production of by-products such as acrolein and allyl alcohol be minimized because both compounds are highly toxic and cause irritation to the eyes and mucous membranes. According to the process of the invention, the amount of acrolein contained in the condensate exiting the ester exchange column is no greater than 700 ppm, preferably no greater than 350 ppm, and more preferably no greater than 30 ppm. The amount of allyl alcohol contained in the condensate exiting the ester exchange column is no greater than 1000 ppm, preferably no greater than 400 ppm, and more preferably no greater than 200 ppm. The term "ppm" is used herein to mean parts per million and is equal to micrograms per gram.

The liquid reaction product containing bis(3-hydroxypropyl) terephthalate monomer and low molecular weight oligomers of 1,3-propanediol and terephthalic acid are removed from the ester exchange vessel via outlet 13 in the calandria 6. The liquid reaction product contains unreacted dimethylterephthalate in an amount not greater than 9%, preferably not greater than 4%, of the total weight of the exit stream. The monomer/oligomer mixture may be fed to a prepolymerizer, flasher or other reaction vessel where it is further reacted to produce a higher molecular weight poly (1,3-propylene terephthalate) prepolymer.

The residence time in the ester exchange column is about 1 to 2 hours.

EXAMPLES 1–7

Using an ester exchanger of the type indicated in the drawings, a 76.4 lb./hr (34.7 kg/hr) stream of dimethyl terephthalate (DMT) was preheated to a temperature of 185° C. and continuously mixed with a stream of catalyzed 1,3-propanediol which was also preheated to a temperature of 185° C., to form a mixture. The mole ratio of 1,3-propanediol to dimethylterephthalate was varied from 1.5:1 to 1.8:1 to 2.0:1 to 2.25:1 by varying the catalyzed 1,3- propanediol stream from 44.9 lb./hr (20.4 kg/hr) to 53.9 lb./hr (24.5 kg/hr) to 59.9 lb./hr (27.2 kg/hr) to 67.3 lb./hr (30.6 kg/hr). The catalyst was tetraisopropyl titanate (Tyzor® TPT, available from E. I. du Pont de Nemours and Company, Wilmington, Del.), which was added to the glycol in an amount sufficient to yield 50 ppm or 30 ppm by weight of titanium based on the weight of poly(1,3-propylene terephthalate) formed in subsequent processing. The dimethylterephthalate/catalyzed glycol mixture was fed into the ester exchanger either at the base (calandria) or at the quarterpoint. The temperature of the liquid reactants at the base of the ester exchanger (calandria) was maintained at 237° C., and the pressure at the base of the ester exchanger was maintained at 900 to 950 mm Hg (119,970 to 126,635 Pa). The pressure at the top of the ester exchange column was atmospheric. In the ester exchanger, the 1,3-propanediol reacted with the dimethylterephthalate to form bis(3-hydroxypropyl) terephthalate monomer and low molecular weight oligomers of 1,3-propanediol and terephthalic acid, liberating methanol vapor and other by-products, which were continuously removed from the top of the ester exchanger. The monomer/oligomer mixture was continuously removed from the base of the ester exchanger to be fed to a prepolymerizer, flasher or other reaction vessel where it was further reacted to produce poly(1,3-propylene terephthalate) prepolymer. The conditions and results for the continuous ester exchange process are set forth in Table I.

In Table I, the level of catalyst is given as parts per million (ppm) by weight of titanium in the finished polymer. The amount of unconverted dimethylterephthalate (DMT) is given as a weight percentage based upon the total weight of the exit stream. The acrolein and allyl alcohol levels are given in parts per million (ppm) by weight based on the total condensate that is removed from the ester exchange vessel. The dipropylene glycol (DPG) levels are given as a weight percent based on monomer/oligomer exiting the exchange vessel.

TABLE I

| Example | Catalyst Ti (ppm) | Mole Ratio Glycol/DMT | Unconv. DMT (wt. %) | Acrolein (ppm) | Allyl Alcohol (ppm) | DPG (wt. %) |
| --- | --- | --- | --- | --- | --- | --- |
| 1 | 50 | 1.5* | 5.6 | 76 | 506 | 0.12 |
| 2 | 50 | 1.5 | 5.6 | 22 | 291 | 0.13 |
| 3 | 50 | 1.8 | 5.8 | 37 | 259 | 0.15 |
| 4 | 50 | 2.0* | 3.4 | 37 | 202 | 0.25 |
| 5 | 50 | 2.0 | 4.5 | 31 | 222 | 0.19 |
| 6 | 50 | 2.25 | 5.3 | 21 | 146 | 0.19 |
| 7 | 30 | 1.5 | 7.1 | 20 | 246 | 0.13 |

*In Examples 1 and 4, 1,3-propanediol (glycol) and dimethylterephthalate (DMT) were premixed and fed to the ester exchanger vessel at the quarter point. In all other Examples, the 1,3-propanediol/dimethylterephthalate mixture was fed to the base of exchanger.

What is claimed is:

1. A process for the continuous production of at least one of bis(3-hydroxypropyl) terephthalate and low molecular weight oligomers of 1,3-propanediol and terephthalic acid, comprising:
   (a) preheating 1,3-propanediol to a temperature of about 150° C. to about 200° C.;
   (b) preheating one or more lower dialkyl esters of terephthalic acid to a temperature of about 150° C. to about 220° C.;
   (c) combining the preheated 1,3-propanediol with the preheated terephthalic acid ester to form a mixture having a mole ratio of 1,3-propanediol to terephthalic acid ester of about 1.2:1 to about 2.3:1 and maintaining the temperature of the mixture at about 150° C. to about 220° C.;
   (d) continuously feeding the preheated 1,3-propanediol/terephthalic acid ester mixture through at least one inlet to an ester exchange vessel where the mixture undergoes a continuous transesterification reaction to form a liquid reaction mixture and gaseous reaction products;
   (e) continuously heating and mixing the liquid reaction mixture, whereby the temperature of the mixture in a base portion of the ester exchange vessel is maintained at about 215° C. to about 250° C. and the pressure in a base portion of the ester exchange vessel is maintained at about 800 mm Hg to about 1,000 mm Hg, thereby continuing the transesterification reaction to form liquid reaction products and gaseous reaction products;
   (f) continuously separating the gaseous reaction products from the liquid reaction mixture in a separating portion of the ester exchange vessel which is above the base portion; and
   (g) continuously removing a stream of liquid reaction products from the base portion of the ester exchange vessel, the stream comprising at least one of bis(3-hydroxypropyl) terephthalate and low molecular weight oligomers of 1,3-propanediol and terephthalic acid.

2. The process according to claim 1, wherein the terephthalic acid ester is dimethylterephthalate.

3. The process according to claim 1, wherein a transesterification catalyst is mixed with the 1,3-propanediol prior to the preheating step.

4. The process according to claim 3, wherein the transesterification catalyst is selected from the group consisting of organic or inorganic compounds of titanium, lanthanum, zinc and cobalt.

5. The process according to claim 1, wherein the separated gaseous reaction products are condensed, and the condensate contains not greater than 700 ppm of acrolein and not greater than 1000 ppm allyl alcohol, based on total condensates.

6. The process according to claim 1, wherein the condensed gaseous reaction products contain not greater than 350 ppm of acrolein and not greater than 400 ppm allyl alcohol, based on total condensates.

7. The process according to claim 1, wherein the condensed gaseous reaction products contain not greater than 30 ppm of acrolein and not greater than 200 ppm allyl alcohol, based on total condensates.

8. The process according to claim 1, wherein the mixture that is fed to the ester exchange vessel has a mole ratio of the 1,3-propanediol to terephthalic acid ester of about 1.3:1 to about 1.7:1.

9. The process according to claim 1, wherein said at least one of bis(3-hydroxypropyl) terephthalate and low molecular weight oligomers have an average degree of polymerization of about 1 to about 15.

10. The process according to claim 1, wherein the 1,3-propanediol and the terephthalic acid esters are each preheated to a temperature of about 185° C.

11. The process according to claim 1, wherein the mixture in the base portion of the ester exchange vessel is heated to a temperature of about 230° C. to about 240° C.

12. The process according to claim 1, wherein the pressure in the base portion of the ester exchange vessel is maintained at about 850 mm Hg to about 950 mm Hg.

13. The process according to claim 1, wherein the stream of liquid reaction products that is removed from the ester exchange vessel contains unreacted terephthalic acid ester in an amount not greater than 9 weight percent.

14. The process according to claim 1, wherein the stream of liquid reaction products that is removed from the ester exchange vessel contains unreacted terephthalic acid ester in an amount not greater than 4 weight percent.

15. The process according to claim 1, wherein the ester exchange vessel comprises a bubble cap column having a plurality of bubble cap plates spaced vertically apart from one another.

16. The process according to claim 1, wherein said at least one inlet is located below the midpoint of the ester exchange vessel.

17. The process according to claim 1, wherein said at least one inlet is located in a base portion of the ester exchange vessel.

18. The process according to claim 1, wherein a stream of the liquid reaction mixture is withdrawn from a base portion of the ester exchange vessel, the withdrawn mixture is heated by being passed through the external heater, and the withdrawn heated mixture is fed back to the base portion causing the mixing.

19. The process according to claim 1, further comprising the steps of: condensing the separated gaseous reaction products into a liquid state; and feeding at least a portion of the condensed gaseous reaction products to an upper portion of the ester exchange vessel.

20. A process for the continuous production of at least one of bis(3-hydroxypropyl) terephthalate and low molecular weight oligomers of 1,3-propanediol and terephthalic acid, comprising:
(a) preheating a mixture of 1,3-propanediol and at least one transesterification catalyst to a temperature of about 150° C. to about 200° C.;
(b) preheating dimethylterephthalate to a temperature of about 150° C. to about 220° C.;
(c) combining the preheated 1,3-propanediol and catalyst with the preheated dimethylterephthalate to form a mixture having a mole ratio of 1,3-propanediol to dimethylterephthalate of about 1.2:1 to about 2.3:1 and maintaining the temperature of the mixture at about 150° C. to about 220° C.;
(d) continuously feeding the preheated 1,3-propanediol/catalyst/dimethylterephthalate mixture through an inlet to an ester exchange vessel where the mixture undergoes a continuous transesterification reaction to form a liquid reaction mixture and gaseous reaction products, wherein said inlet is located at or below about the midpoint of the ester exchange vessel;
(e) continuously heating and mixing the liquid reaction mixture, whereby the temperature of the mixture in a base portion of the ester exchange vessel is maintained at about 215° C. to about 250° C. and the pressure in a base portion of the ester exchange vessel is maintained at about 800 mm Hg to about 1,000 mm Hg, thereby continuing the transesterification reaction to form liquid reaction products and gaseous reaction products;
(f) continuously separating the gaseous reaction products from the liquid reaction mixture in a separating portion of the ester exchange vessel which is above the base portion, and continuously condensing the separated gaseous reaction products, wherein the condensate contains not greater than 350 ppm of acrolein and not greater than 400 ppm allyl alcohol, based on total condensates; and
(g) continuously removing a stream of liquid reaction products from the base portion of the ester exchange vessel, the stream comprising at least one of bis(3-hydroxypropyl) terephthalate and low molecular weight oligomers of 1,3-propanediol and terephthalic acid having an average degree of polymerization of about 1 to about 15 and unreacted terephthalic acid ester in an amount not greater than 9 percent by weight of the stream.

21. The process according to claim 1, wherein said at least one inlet is located at or below about the midpoint of the ester exchange vessel.

22. The process according to claim 20, wherein said at least one inlet is located below the midpoint of the ester exchange vessel.

23. The process according to claim 20, wherein the ester exchange vessel comprises a bubble cap column having a plurality of bubble cap plates spaced vertically apart from one another.

24. The process according to claim 15, wherein said at least one inlet is located at or below about the midpoint of the bubble cap column.

25. The process according to claim 23, wherein said at least one inlet is located at or below about the midpoint of the bubble cap column.

26. The process according to claim 20, wherein (a) the terephthalic acid ester is dimethylterephthalate, (b) a transesterification catalyst is mixed with the 1,3-propanediol prior to the preheating step, and (c) the transesterification catalyst is selected from the group consisting of organic or inorganic compounds of titanium, lanthanum, zinc and cobalt.

27. A process for the continuous production of at least one of bis(3-hydroxypropyl) terephthalate and low molecular weight oligomers of 1,3-propanediol and terephthalic acid, comprising:
(a) preheating 1,3-propanediol to a temperature of about 150° C. to about 200° C.;
(b) preheating one or more lower dialkyl esters of terephthalic acid to a temperature of about 150° C. to about 220° C.;
(c) combining the preheated 1,3-propanediol with the preheated terephthalic acid ester to form a mixture having a mole ratio of 1,3-propanediol to terephthalic acid ester of about 1.2:1 to about 2.3:1 and maintaining the temperature of the mixture at about 150° C. to about 220° C.;
(d) continuously feeding (1) the preheated 1,3-propanediol/terephthalic acid ester mixture through at least one inlet to an ester exchange vessel and (2) continuously feeding additional 1,3-propanediol through a separate inlet to the exchange vessel where the total 1,3-propanediol and terephthalic acid added to the ester exchange vessel is in a mole ratio of 1,3-propanediol to terephthalic acid ester of about 1.2:1 to about 2.3:1 and the 1,3-propanediol and terephthalic acid undergo a continuous transesterification reaction to form a liquid reaction mixture and gaseous reaction products;
(e) continuously heating and mixing the liquid reaction mixture, whereby the temperature of the mixture in a base portion of the ester exchange vessel is maintained at about 215° C. to about 250° C. and the pressure in a base portion of the ester exchange vessel is maintained at about 800 mm Hg to about 1,000 mm Hg, thereby continuing the transesterification reaction to form liquid reaction products and gaseous reaction products;

(f) continuously separating the gaseous reaction products from the liquid reaction mixture in a separating portion of the ester exchange vessel which is above the base portion; and (g) continuously removing a stream of liquid reaction products from the base portion of the ester exchange vessel, the stream comprising at least one of bis(3-hydroxypropyl) terephthalate and low molecular weight oligomers of 1,3-propanediol and terephthalic acid.

28. The process according to claim 27, wherein the continuously feeding (1) the preheated 1,3-propanediol/terephthalic acid ester mixture is injected through an inlet in the base of the ester exchange vessel and (2) the additional 1,3-propanediol is injected at an inlet at about the quarter point of the ester exchange vessel.

29. A process for the continuous production of at least one of bis(3-hydroxypropyl) terephthalate and low molecular weight oligomers of 1,3-propanediol and terephthalic acid, comprising:

(a) preheating 1,3-propanediol to a temperature of about 150° C. to about 200° C.;

(b) preheating one or more lower dialkyl esters of terephthalic acid to a temperature of about 150° C. to about 220° C.;

(c) continuously feeding the preheated 1,3-propanediol and the preheated terephthalic acid ester to an ester exchange vessel through separate inlets located at or below about the midpoint of the ester exchange vessel in a mole ratio of 1,3-propanediol to terephthalic acid ester of about 1.2:1 to about 2.3:1 and where the 1,3-propanediol and the terephthalic acid ester undergo a continuous transesterification reaction to form a liquid reaction mixture and gaseous reaction products;

(d) continuously heating and mixing the liquid reaction mixture, whereby the temperature of the mixture in a base portion of the ester exchange vessel is maintained at about 215° C. to about 250° C. and the pressure in a base portion of the ester exchange vessel is maintained at about 800 mm Hg to about 1,000 mm Hg, thereby continuing the transesterification reaction to form liquid reaction products and gaseous reaction products;

(e) continuously separating the gaseous reaction products from the liquid reaction mixture in a separating portion of the ester exchange vessel which is above the base portion; and (f) continuously removing a stream of liquid reaction products from the base portion of the ester exchange vessel, the stream comprising at least one of bis(3-hydroxypropyl) terephthalate and low molecular weight oligomers of 1,3-propanediol and terephthalic acid.

30. The process according to claim 29, wherein the inlet where the preheated terephthalic acid ester is injected is in the base of the ester exchange vessel and the inlet where the preheated 1,3-propanediol is injected is at about the quarter point of the ester exchange vessel.

31. The process according to claim 29, wherein a transesterification catalyst is added to the 1,3-propanediol prior to its injection into the ester exchange vessel.

32. A process for the continuous production of at least one of bis(3-hydroxypropyl) terephthalate and low molecular weight oligomers of 1,3-propanediol and terephthalic acid, comprising:

(a) preheating 1,3-propanediol to a temperature of about 150° C. to about 200° C.;

(b) preheating one or more lower dialkyl esters of terephthalic acid to a temperature of about 150° C. to about 220° C.;

(c) continuously feeding the preheated 1,3-propanediol and the preheated terephthalic acid ester through at least one inlet to an ester exchange vessel located at or below about the midpoint of the ester exchange vessel where the total 1,3-propanediol and terephthalic acid added to the ester exchange vessel is in a mole ratio of 1,3-propanediol to terephthalic acid ester of about 1.2:1 to about 2.3:1 and the 1,3-propanediol and terephthalic acid undergo a continuous transesterification reaction to form a liquid reaction mixture and gaseous reaction products;

(d) continuously heating and mixing the liquid reaction mixture, whereby the temperature of the mixture in a base portion of the ester exchange vessel is maintained at about 215° C. to about 250° C. and the pressure in a base portion of the ester exchange vessel is maintained at about 800 mm Hg to about 1,000 mm Hg, thereby continuing the transesterification reaction to form liquid reaction products and gaseous reaction products;

(e) continuously separating the gaseous reaction products from the liquid reaction mixture in a separating portion of the ester exchange vessel which is above the base portion; and (f) continuously removing a stream of liquid reaction products from the base portion of the ester exchange vessel, the stream comprising at least one of bis(3-hydroxypropyl) terephthalate and low molecular weight oligomers of 1,3-propanediol and terephthalic acid.

33. The process according to claim 32, wherein the ester exchange vessel comprises a bubble cap column having a plurality of bubble cap plates spaced vertically apart from one another and said at least one inlet is located at or below about the midpoint of the bubble cap column, the terephthalic acid ester is dimethylterephthalate, a transesterification catalyst is mixed with the 1,3-propanediol prior to the preheating step, and the transesterification catalyst is selected from the group consisting of organic or inorganic compounds of titanium, lanthanum, zinc and cobalt.

* * * * *